(12) United States Patent
Lindner et al.

(10) Patent No.: US 12,156,948 B2
(45) Date of Patent: Dec. 3, 2024

(54) ABSORBENT ARTICLE WITH THREE-DIMENSIONAL HOT-MELT BONDED LAMINATE

(71) Applicant: The Procter & Gamble Company, Cincinnati, OH (US)

(72) Inventors: Torsten Lindner, Kronberg (DE); Gueltekin Erdem, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 532 days.

(21) Appl. No.: 16/843,322

(22) Filed: Apr. 8, 2020

(65) Prior Publication Data

US 2020/0330291 A1  Oct. 22, 2020

(51) Int. Cl.
*A61L 15/24* (2006.01)
*A61F 13/15* (2006.01)
*A61F 13/51* (2006.01)
(Continued)

(52) U.S. Cl.
CPC ......... *A61L 15/24* (2013.01); *A61F 13/51104* (2013.01); *A61F 13/5125* (2013.01); *A61F 13/514* (2013.01); *A61F 13/515* (2013.01); *A61F 13/532* (2013.01); *A61F 13/55105* (2013.01); *A61L 15/42* (2013.01); *D04H 1/02* (2013.01); *D04H 1/4266* (2013.01); *D04H 1/43835* (2020.05); *D04H 1/5405* (2013.01); *D04H 1/58* (2013.01); *D04H 1/593* (2013.01); *A61F 2013/15325* (2013.01); *A61F 2013/15406* (2013.01); *A61F 2013/15569* (2013.01); *A61F 2013/15861* (2013.01); *A61F 2013/51019* (2013.01); *A61F 2013/5103* (2013.01); *A61F 2013/51038* (2013.01); *A61F 13/534* (2013.01);
(Continued)

(58) Field of Classification Search
None
See application file for complete search history.

(56) References Cited

U.S. PATENT DOCUMENTS 5,882,769 A    3/1999  Mccormack et al.
6,809,048 B1 * 10/2004  Jacobs ............. A61F 13/51476
                                                     428/196
(Continued)

FOREIGN PATENT DOCUMENTS

CN    208710282 U    4/2019
CN    209596061 U    11/2019
(Continued)

OTHER PUBLICATIONS

International Search Report and Written Opinion; Application Ser. No. PCT/CN2019/082955; dated Jan. 15, 2020; 8 pages.

*Primary Examiner* — Arti Singh-Pandey
(74) *Attorney, Agent, or Firm* — Daniel S. Albrecht

(57) ABSTRACT

An absorbent article such as a baby diaper comprising a three-dimensional laminate 30 having a first layer 1 intermittently bonded to a second layer 2 by a heterophase polymer. The topsheet comprises three-dimensional protrusions 9 in the first layer 1 which are not bonded to the second layer 2. The heterophase polymer has an enthalpy of fusion of at least 10 J/g. The laminate may be used on the wearer-facing side of the article as topsheet 24 and/or on the garment-facing side as part of the backsheet 26. The first layer may comprise natural fibers.

17 Claims, 6 Drawing Sheets

(51) Int. Cl.

| | | |
|---|---|---|
| *A61F 13/511* | (2006.01) | |
| *A61F 13/512* | (2006.01) | |
| *A61F 13/514* | (2006.01) | |
| *A61F 13/515* | (2006.01) | |
| *A61F 13/532* | (2006.01) | |
| *A61F 13/534* | (2006.01) | |
| *A61F 13/539* | (2006.01) | |
| *A61F 13/551* | (2006.01) | |
| *A61L 15/42* | (2006.01) | |
| *D04H 1/02* | (2006.01) | |
| *D04H 1/4266* | (2012.01) | |
| *D04H 1/4382* | (2012.01) | |
| *D04H 1/54* | (2012.01) | |
| *D04H 1/58* | (2012.01) | |
| *D04H 1/593* | (2012.01) | |

(52) U.S. Cl.
CPC .............. *A61F 2013/5349* (2013.01); *A61F 2013/5395* (2013.01); *Y10T 442/68* (2015.04)

(56) References Cited

U.S. PATENT DOCUMENTS

| | | | |
|---|---|---|---|
| 9,200,185 B2 † | 12/2015 | Knutson | |
| 9,469,791 B2 † | 10/2016 | Knutson | |
| 2011/0313385 A1 | 12/2011 | Hammons et al. | |
| 2014/0079919 A1* | 3/2014 | Bunnelle | C09J 7/35 |
| | | | 525/240 |
| 2014/0121626 A1 | 5/2014 | Finn et al. | |
| 2016/0074251 A1 | 3/2016 | Strube et al. | |
| 2016/0074253 A1 | 3/2016 | Strube et al. | |
| 2016/0256592 A1 | 9/2016 | Lindner et al. | |
| 2017/0165396 A1 | 6/2017 | Turner | |
| 2017/0204306 A1 | 7/2017 | Wang et al. | |
| 2017/0209616 A1 | 7/2017 | Turner | |
| 2018/0002579 A1 | 1/2018 | Hu | |

FOREIGN PATENT DOCUMENTS

| | | |
|---|---|---|
| JP | 2004000465 A | 1/2004 |
| JP | 2015533623 A | 11/2015 |
| WO | WO2015134359 A1 | 9/2015 |
| WO | WO2015134371 A1 | 9/2015 |
| WO | WO2015134375 A1 | 9/2015 |
| WO | WO2015191802 A1 | 12/2015 |
| WO | 2017106151 A1 † | 6/2017 |
| WO | WO2017156200 A1 | 9/2017 |
| WO | WO2017156203 A1 | 9/2017 |
| WO | 2018160161 A1 | 9/2018 |

\* cited by examiner
† cited by third party

ABSORBENT ARTICLE WITH THREE-DIMENSIONAL HOT-MELT BONDED LAMINATE

CROSS REFERENCE TO RELATED APPLICATION

This application claims priority under 35 U.S.C. § 119 to Chinese Patent Application Serial No. 2019/082955, filed on Apr. 17, 2019, the entire disclosure of which is hereby incorporated by reference.

FIELD OF THE INVENTION

The invention is for an absorbent article such as a baby diaper, a training pant, a feminine hygiene sanitary napkin or an adult incontinence product. The article of the invention comprises a three-dimensional laminate, which may be disposed on the wearer-facing side or the garment-facing side of the article. The laminate comprises a first layer which is intermittently bonded to a second layer by a hot-melt adhesive. The first layer comprises a plurality of protrusions not bonded to the second layer.

BACKGROUND OF THE INVENTION

Absorbent articles for personal hygiene, such as disposable diapers for infants, training pants for toddlers, adult incontinence undergarments and/or sanitary napkins are designed to absorb and contain body exudates, in particular large quantities of urine, runny bowel movement (BM) and/or menses. These absorbent articles comprise several layers providing different functions. A liquid permeable topsheet is disposed closest to the wearer's skin and should be capable of quickly absorbing the excreted fluid. A liquid impermeable backsheet is disposed on the opposed, garment-facing side of the article. The backsheet typically comprises a liquid impermeable film, and may optionally further comprises an externally-facing nonwoven attached in face-to-face relation with the film to improve the feel of the backsheet. Other components of absorbent articles are well known, and include in particular an absorbent core disposed between the topsheet and the backsheet to absorb and retain the excreted fluids.

Topsheets having a three-dimensional texture have been suggested to reduce skin fluid contact and/or skin fluid contact time during a urination event. WO2017/106151A1 (Turner, P&G) for example discloses topsheet laminates comprising a morphological treatment, wherein the layers of the laminates are bonded with a substantially tackifier-free adhesive. Tackifiers are indicated to potentially create migration and instability issue that negatively affect the performance and consumer impression of the article among other drawbacks. The substantially tackifier-free adhesive of Turner comprises an amorphous polyolefin composition and either a heterophase polymer or a second amorphous polymer comprising at least one butene monomer.

It is desirable to provide absorbent articles that are soft to the touch. Additionally, it may be desirable to use natural fibers. Natural fibers however do not behave like the synthetic fibers of conventional topsheets and require new developments to ensure good level of performance.

SUMMARY OF THE INVENTION

The present invention is directed to an absorbent article comprising a three-dimensional laminate comprising a first layer and a second layer. The first layer is intermittently bonded to the second layer by a hot-melt adhesive so that the first layer comprises a plurality of protrusions not bonded to the second layer. The hot-melt adhesive comprises more than 90% by weight of a heterophase polymer having an enthalpy of fusion of at least 10 J/g, as measured according to the Enthalpy of Fusion Measurement Method described herein. The enthalpy of fusion may advantageously be in the range of from 15 J/g to 40 J/g. The adhesive may in particular consist essentially of the heterophase polymer, and optionally a minor amount of additives, such as stabilizer (antioxidants), optical brighteners, plasticizers, pigments etc. . . . . . An example of suitable heterophase polymers are propylene-ethylene copolymers. The hot-melt adhesive is advantageously free of tackifiers, which are used in conventional hot-melt adhesives.

The laminate may be disposed on the wearer-facing side of the article or on the garment-facing side of the article. The first layer is advantageously disposed outwardly, and the second layer disposed inwardly, so that the protrusions can provide a soft touch to the external surface of the article. The invention may be embodied in different aspects, indicated below, which are however not limiting the invention.

According to a first aspect, the three-dimensional laminate is disposed on the wearer-facing side of the article, and the laminate may form part of, or the whole of, the topsheet. In this first aspect, the first layer may in particular comprise natural fibers, in particular from 15 w. % and up to 100 w. % of natural fibers.

According to a second aspect, the three-dimensional laminate is disposed on the wearer-facing side of the article, and may form part, or the whole of, the topsheet. The hot-melt adhesive, which comprises more than 90% by weight of a heterophase polymer having an enthalpy of fusion of at least 10 J/g measured according to the Enthalpy of Fusion Measurement Method described herein, may in particular be free of styrene block copolymers.

According to a third aspect, the laminate is disposed on the wearer-facing side of the article and/or on the garment-facing side of the article, and the hot-melt adhesive has a storage modulus (G') higher than $0.3 \times 10^6$ at 37° C. (reflecting in-use conditions). The relative high G' value is indicative of an adhesive that is not tacky in this range of temperature, which enables the three-dimensional structures to be maintained against any tack-down, which are typically present while the laminate is kept under pressure in a rolled form, or during the making process or in the packaging of the absorbent articles. This prevents the first layer from being inadvertently bonded to the second layer in the area of the protrusions.

According to another aspect, the invention is also for an absorbent article comprising a laminate disposed on the garment-facing side of the article, wherein the laminate comprises a first layer, a second layer, the first layer being intermittently bonded to the second layer by a hot-melt adhesive so that the first layer comprises a plurality of protrusions not bonded to the second layer (2), and wherein the adhesive has a storage modulus (G') higher than $0.3 \times 10^6$ Pa at 37° C.

The article is illustrated in the Figures as a taped diaper. For ease of discussion, the absorbent article and the laminate will be discussed with reference to the numerals referred to in these Figures. The Figures and detailed description should however not be considered limiting the scope of the claims, unless explicitly indicated otherwise. In particular, the invention may also be used in a wide variety of absorbent article forms, such as pant type diapers, which are preformed and are worn like an underwear garment, or female protection sanitary pads.

DETAILED DESCRIPTION OF THE INVENTION

Definitions of Terms

Figure 1:
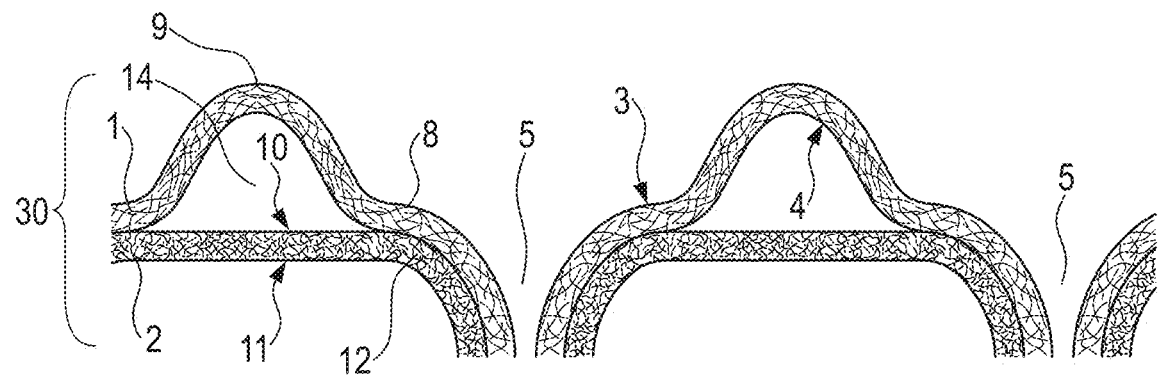
FIG. 1 is a schematic cross-sectional view of a laminate in accordance with the present invention having protrusions and apertures.

The term "absorbent article" as used herein refers to disposable products such as taped diapers, diapers having a closed waist opening (pants), feminine hygiene sanitary napkins and the like, which are placed against or in proximity to the body of the wearer to absorb and contain bodily exudates such as urine, feces or menses discharged from the body. Typical absorbent articles comprise a topsheet, a backsheet, an absorbent core, an acquisition layer and other components. The liquid permeable topsheet forms at least a portion of the wearer-facing side of the article, and the liquid impermeable backsheet forms at least a portion, and typically the whole, of the garment-side of the article. The articles may be provided with fastening elements, such as tapes (taped diapers) or may be provided already pre-formed with a waist opening and a pair of leg openings as in an underwear (pant diapers). The absorbent articles may be for use with babies, infants, women or incontinent adults. Typical features of absorbent articles are further discussed further below, and in relation with the illustrated taped diaper in FIGS. 4-6, which is of course for illustration purpose only and not limiting the scope of the inventions, unless specifically indicated otherwise.

The term "nonwoven" as used herein refers to a manufactured material, web, sheet or batt of directionally or randomly oriented fibers, bonded by friction, and/or cohesion and/or adhesion, excluding paper and products which are woven, knitted, tufted, stitch-bonded, incorporating binding yarns or filaments, or felted by wet milling, whether or not additionally needled. The fibers may be of natural or man-made origin. The fibers may be staple or continuous filaments or be formed in situ. The porous, fibrous structure of a nonwoven may be configured to be liquid permeable or impermeable, as desired.

The term "spunlace nonwoven" means a nonwoven wherein the cohesion and the interlacing of the fibers with one another is obtained by means of a plurality of jets of water under pressure passing through a moving fleece or cloth and, like needles, causing the fibers to intermingle with one another. These spunlace nonwovens are essentially defined by the fact that their consolidation results from hydraulic interlacing. "Spunlace nonwoven", as used herein, also relates to a nonwoven formed of two webs, which are combined with each other by hydraulic interlacing. The two webs, prior to being combined into one nonwoven by hydraulic interlacing, may have underdone bonding processes, such as heat and/or pressure bonding by using e.g. a patterned calendar roll and an anvil roll to impart a bonding pattern. However, the two webs are combined with each other solely by hydraulic interlacing.

"Comprise," "comprising," and "comprises" are open ended terms, each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essential of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "advantageously" and the likes also qualify features which are not intended to limit the scope of the claims unless specifically indicated to do so.

Three-Dimensional Laminate 30, 30' with First Layer 1 and Second Layer 2

The three-dimensional laminate layer 30 (herein more simply referred to as "the laminate") of the invention comprises a first layer 1 and a second layer 2. While the first layer 1 and the second layer 2 will be discussed individually in greater details in dedicated sections further below, this section will briefly discuss the laminate 30 comprising these two layers, as a whole.

The laminate 30 can be used in any part of the absorbent article, in particular on the wearer-facing side 24 and/or the garment-facing side of the article 26. The wearer-facing side of the article is the side that is in contact with the wearer's skin during use of the article. The wearer-facing side is at least partially formed by a liquid permeable topsheet, which may thus be, at least partially, a laminate 30 according to the invention. In the Figures, the wearer-facing side of the article and the topsheet layer are referred to by the same number 24. The absorbent article comprises a garment-facing side on the opposite side of the article, which is typically formed by a liquid impermeable backsheet 26. The laminate of the invention may be used on the garment-facing side alone or in combination with a liquid impermeable film to provide a backsheet having an improved feel. In the Figures, the garment-facing side of the article and the backsheet layer are referred to by the same number 26.

Figure 2:
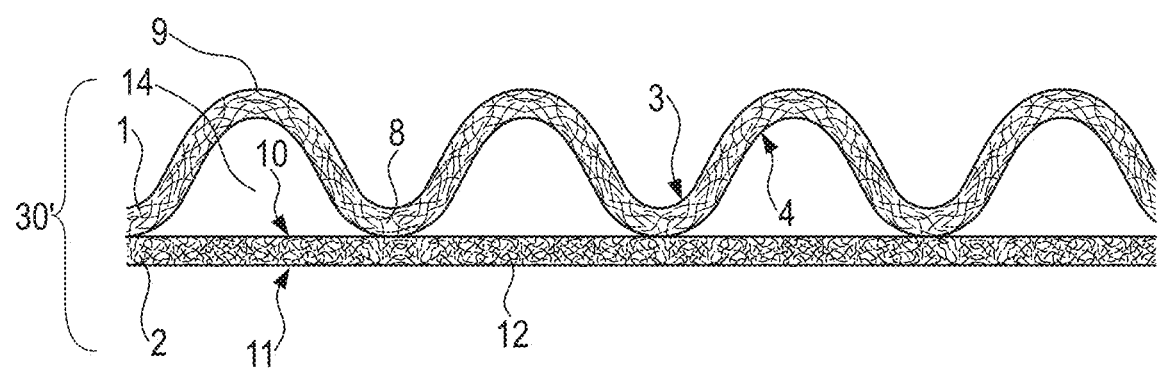
FIG. 2 is schematic cross-sectional view of an alternative topsheet laminate in accordance with the present invention without apertures.

FIG. 1 and FIG. 2 schematically show a cross-section of two exemplary laminates 30, 30' according to the invention. The laminate comprises a three-dimensional first layer 1 and a second layer 2. The first layer 1 and the second layer 2 are disposed in a face to face relationship. The first layer 1 comprises a first surface 3 and a second surface 4. The second layer 2 comprises a first surface 10 and a second surface 11. The first surface 10 of the second layer 2 faces the second surface 4 of the first layer 1. The first surface 3 of the first layer 1 and the first surface 10 of the second layer 2 are typically facing outwardly (externally), for example towards the wearer-facing side of the article, while the second surface 4 of the first layer 1 and the second surface 11 of the second layer 2 are typically facing inwardly (internally), when the laminate is incorporated in an absorbent article.

According to the present invention, the first layer 1 is intermittently bonded to the second layer 2. The first layer 1 forms a plurality of protrusions 9 which are unbonded to the second layer 2. The protrusions 9 provide a three-dimensional profile to the first layer 1 and more generally to the laminate as a whole. The first layer 1 and the second layer 2 may be generally contiguous in the horizontal plane, but it is not excluded that the second layer may be wider or longer than the first layer. For example, the second layer may form a secondary topsheet or an acquisition layer that covers a larger area than the first layer. In this example, the first layer may have a smaller area disposed in the central region of the article, relative to the second layer. The protrusions may also be present only in a selected area of the laminate that is smaller than the overall surface of the laminate.

FIG. 1 shows a laminate 30 further comprising apertures 5 extending through the first layer 1 and the second layer 2. Laminates comprising apertures may be in particular used as topsheet 24, or at least to form at least a portion of the topsheet. The apertures 5 in the first layer of the topsheet enable initial and fast fluid flow, especially when the first layer is hydrophobic. Therefore, the first layer of the topsheet, which may be hydrophobic, works in concert with the apertures to reduce wetness on the wearer-facing surface of the topsheet. Such a dual layer topsheet construction is disclosed for example in WO2015/134359 A1 (Isele at al., P&G) and PCT application CN2018/110397 filed Oct. 16, 2018 (Erdem et al, P&G). Such apertured laminates may also be disposed on the garment-facing side of the article, especially when attached to a liquid-impermeable polymeric film, to form a liquid impermeable composite backsheet 26.

Laminates 30', such as in FIG. 2, which do not comprise apertures crossing through the laminate may also be disposed on the wearer-facing side, or on the garment facing side of the article. Such a laminate 30' may in particular be used to form at least a portion of, or the whole of, the garment-facing side of the article. For example such laminate 30' may be attached to a liquid-impermeable polymeric film to form a composite backsheet 26. A laminate 30' without apertures, as schematically shown in FIG. 2, may also be used as topsheet. In this case, the fibers forming the first and second layers are advantageously not hydrophobically treated.

The laminate including the first layer and second layer may typically have a basis weight from 15 g/m$^2$ to 80 g/m$^2$, or from 15 g/m$^2$ to 60 g/m$^2$, or from 20 g/m$^2$ to 50 g/m$^2$. The first layer may have a basis weight of from 10 g/m$^2$ to 50 g/m$^2$, or from 15 g/m$^2$ to 40 g/m$^2$. The second layer may have a basis weight of from 5 g/m$^2$ to 50 g/m$^2$, or from 7 g/m$^2$ to 30 g/m$^2$, or from 7 g/m$^2$ to 20 g/m$^2$. The second layer may have a basis weight that is at least 5 g/m$^2$ lower, or at least 10 g/m$^2$ lower, than the basis weight of the first layer. It has been found that such relatively low basis weight layers are sufficient to facilitate stabilization of the three-dimensional configuration of the first layer. The laminate typically comprise only the first and second layers, but it is not excluded that a third or more layers may also be present in the laminate, for example between the first layer and second layer, or on the second surface of the second layer.

The laminate may be in close contact with adjacent layers of the article. When the laminate 30 is used on the wearer-facing side 24 of the article, such an adjacent layer may be an acquisition layer 54. When the laminate 30 is used on the garment-facing side 26, such layer may be the absorbent core 28 or a liquid impermeable backsheet film.

Protrusions 9

The plurality of protrusions 9 imparts a three-dimensional shape to the first layer 1 and thus to the laminate 30 as a whole, and will be briefly discussed in this section. For the benefits of conciseness, in the following the term "the protrusions" means "all or a majority of the protrusions". The presence of protrusions 9 can typically improve the softness of the laminate 30, and thus of the wearer-facing side 24 and/or garment-facing side 26 of the article on which it is disposed. The protrusions can also help maintaining the skin of the wearer away from body fluids as they create a space between the skin of the wearer and the rest of the article where the body fluids are absorbed.

Viewed from a cross-sectional view as in FIGS. 1-2, i.e. in a Z-direction, the protrusions may have any suitable shapes, including but not limited to: cylindrical, bulbous-shaped, conical-shaped and mushroom shaped. Viewed from above, the majority of the protrusions may have any suitable shapes, including but not limited to: circular, diamond-shaped, round diamond-shaped, U.S. football-shaped, oval-shaped, clover-shaped, triangular-shaped, tear-drop shaped and elliptical-shaped protrusions. Preferably, the protrusions are dome-shaped, as exemplarily illustrated in the photographs of FIGS. 7-8. The protrusions may have a Z-directional height in the range from about 0.1 mm to about 6.0 mm, preferably from about 0.3 mm to about 4.0 mm, more preferably from about 0.5 mm to about 3.0 mm (measured from the land regions 8 to the top of the protrusions on a sufficient number of protrusions).

The protrusions 9 may be uniformly distributed on the first surface 3 of the first layer 1. The protrusions 9 may be provided throughout the complete surface of the first layer 1 or may only be provided in a portion of the first layer 1. Two or more adjacent protrusions 9 are separated by one or more land areas 8 and optionally one or more apertures 5. The protrusions 9 may be surrounded by a plurality of land areas 8 and/or a plurality of apertures 5. The plurality of apertures 5 are located between the protrusions and will be discussed further below. The protrusions may extend upwardly from land areas 8 of the first layer 1 that form a base and have an opposed distal portion from the land areas 8 forming a peak. The base of the protrusions 9, where each protrusion starts to protrude outwardly from the land areas 8, define a perimeter, which for circular protrusions is the circumference.

The protrusions 9 can be hollow and thus comprise an inside void volume 14 which is the portion of the protrusion which does not comprise any fibers, or at least very little fibers. The void volume 14 can improve the breathability of the topsheet and may also provide void volume to temporarily receive body fluids.

The inside void volume 14 may have a width WD, which is the maximum interior width measured between two side walls of the inner protrusion (or which is the maximum diameter of the side wall of the inner protrusion when the distal portion has a substantially circular shape). The width WD of the protrusions 9 may for example range from 0.5 mm to 15 mm or from 0.5 mm to 10 mm or from 0.5 mm to 5 mm or from 0.5 mm to 3 mm. Measurements of the dimensions of the width of the height of the protrusions 9 can be made on a photomicrograph.

The second layer 2 may be free of protrusions. The area of the second layer which coincides with the protrusions of the first layer, may be substantially flat, or may be flat. When combined with the first layer, a hollow space 14 is thus formed inside the topsheet between the protrusions of the first layer and the second layer.

The first layer 1 and the second layer 2 may be joined with each other at the land areas 8 between the protrusions 9 and/or at the apertures 5. The first layer 1 and the second layer 2 are typically not in contact in the areas of the protrusions 9. The Peel Force (delamination force) between the first layer and the second layer (in dry state) may be higher than 0.15 N/50.8 mm, in particular higher than 0.25N/50.8 mm, as measured according to the Peel Force Measurement Method described herein below. If the delamination force is not high enough, there is a risk that the first layer can be detached from the second layer by the move of the wearer of the absorbent article. Furthermore, it is advantageous to have a laminate 30 that keeps its integrity during in-use conditions, especially when the article has been wetted.

First Layer 1

The laminate 30 of the present invention comprises a first layer 1, which is typically disposed more outwardly than the second layer 2, relative to the article. The first layer is typically a nonwoven web that can be obtained from known processes, such as air laying processes, wetlaid processes, meltblowing processes, spunbonding processes, needle punching processes and carding processes etc. . . . . . The fibers can in particular be formed into a nonwoven web via the spunlacing processes (hydroentangling processes) with water jets. Nonwoven webs comprising substantial amounts of natural fibers cannot be consolidated via heat fusion or thermal bonding. Hence, such nonwoven webs comprising natural fibers are often consolidated into a coherent, stable web by using spunlacing processes with water jets. Such nonwoven webs are referred to as spunlace nonwovens, or more simply "spunlaces". Nonwoven webs comprising natural fibers may be textured, via patterning process for example, to form three-dimensional topsheet with specific aesthetics properties and/or functionality properties. It was found that spunlace nonwovens are more dense than other nonwovens, and thus it is more difficult for an adhesive to penetrate in the layer and create a good bond with another layer.

There is a general desire to increase the content of natural fibers, such as cotton, in absorbent articles, especially in the parts of articles that are in contact with the wearer's skin. The first layer 1 may comprise natural fibers, such as cotton fibers, to improve the softness of the laminate, as well as to increase the amount of biodegradable material used. Using natural fibers for layers on the wearer-facing side of absorbent articles is generally desired. The first layer 1 may thus comprise at least 15% by weight, or at least 30% by weight, or at least 50% by weight, or at least 60% by weight, or at least 75% by weight, or at least 95% by weight of natural fibers, such as cotton fibers, by weight of the first layer. The first layer may also be made of 99% to 100% by weight of natural fibers, such as cotton fibers, by weight of the first layer.

Natural fibers may be selected from the group consisting of wheat straw fibers, rice straw fibers, flax fibers, bamboo fibers, cotton fibers, jute fibers, hemp fibers, sisal fibers, bagasse fibers, hesperaloe fibers, miscanthus, marine or fresh water algae/seaweeds and combinations thereof. Preferably, the natural fibers are selected from the group consisting of cotton fibers, silk fibers, bamboo fibers, or mixtures thereof. Preferably, the natural fibers are cotton fibers. Cotton fibers are natural cellulosic fibers that have good liquid acquisition, good breathability and good softness. Therefore, having a topsheet comprising a first layer of cotton fibers improves the softness of the topsheet while improving the fluid handling properties of the topsheet.

The laminate 30 may also further comprise synthetic fibers, especially in the second layer 2, or mixed with the natural fibers in the first layer. When present, synthetic fibers may be selected from the group consisting of polypropylene, polyethylene, polyester, polyethylene terephthalate, polybutylene terephthalate, polyamide, polylactic acid, and combinations thereof. The first layer may comprise heat fusible fibers, which may be mixed with natural fibers in the first layer of the topsheet. The term "heat fusible fibers" means fibers that when they are heated at a certain temperature, the fibers can fusion bond to other fibers that comprise the same material or different material from the heat fusible fibers.

Natural fibers, such as cotton fibers may have a fiber length distribution of from 8 mm to 30 mm. Due to the number of fibers of relatively short length among the fibers, the risk that these short fibers are drawn out of the spunlace layer (fuzzing) during straining and local elongation of the layer while imparting the protrusions is increased versus layers having synthetic fibers. Also, in use conditions when the natural fibers are in contact with the skin of the wearer, the risk of fuzzing of natural fibers is increased versus synthetic fibers due to friction between the skin and the layer, as the shorter fibers are more prone to fuzzing. The attachment of the first layer to a second layer can help to immobilize the shorter fibers in the first layer, thus reducing the risk of rubbing.

The first layer may further be a cross-lapped spunlace nonwoven layer. The precursor web of the first layer may be, for example, a carded nonwoven web formed by a carding process. Once the fibers web is formed via a carding process, a crosslapper, may be used to form a cross-lapped nonwoven layer. The function of a crosslapper is to accept a lightweight fibrous web and to produce a heavier web by laying the lightweight web in layer During this process, the direction of the fiber web may be altered for instance by 90°. Any crosslapping technology known in the art can be applied to obtain a cross-lapped nonwoven layer. Thereby, a web is obtained which is good mechanical strength in machine direction (MD) and cross-direction (CD). Then, the fibers of the cross-lapped nonwoven layer may be bonded into a spunlace nonwoven. Hydroentanglement uses high-speed jets of water to strike a web of fibers so that the fibers are bonded to each other. Hydroentanglement may be carried out using a dry-laid (carded or air-laid) fiber webs or wet-laid webs as a precursor web. At the end of this process, a cross-lapped spunlace nonwoven layer as a first layer of the topsheet is obtained. Thus, the mechanical strength of the first layer of the topsheet may be increased, as typically nonwoven fabrics have certain process-related degree of fibers orientation in machine direction, which leads to higher mechanical strength in MD versus CD.

Alternatively, the first layer may be a spunlace nonwoven layer composed of a nonwoven carrier web and of a web comprising natural fibers with part of the web comprising natural fibers entering the carrier web. The web comprising natural fibers may be formed on one side of the carrier web. Natural fibers of the natural fiber web may enter the fiber network of the carrier web and interlace with the fiber network. Understandably, the natural fibers may interlace with each other. The carrier web may also interlace with the web comprising natural fibers. The carrier web may be made of different types of synthetic fibers. The carrier web may be made also of cellulosic fibers.

The first layer may be hydrophilic or hydrophobic. The first layer is preferably more hydrophobic than the second layer. In order to have a hydrophobic first layer, a hydrophobic treatment may be applied to the first layer. While non-treated cotton is naturally hydrophobic, bleached cotton fibers are hydrophilic. While hydrophilicity facilitates absorption and penetration of body liquids through the topsheet, such hydrophilic topsheets typically stay rather wet due to residual liquid remaining in the topsheet and liquid passing back into (and through) the topsheet from components underneath the topsheet. Therefore, a topsheet comprising natural fibers may be treated with a hydrophobic treatment in order to improve the dryness of the topsheet.

The hydrophobic treatment may be based on synthetic material, at least to some extent, derived from natural sources. The hydrophobic treatment may be based on a natural compound, such as selected from the group consisting of natural oil, butters or waxes and combination thereof. Some examples, but not limited to, are cotton seed oil, Coconut oil, Avocado oil, Jojoba oil, Castor-seed oil, Soybean oil, Almond oil, Lanolin, Olive oil, Sunflower seed oil, Eucalyptus oil, Shea butter, Cocoa butter, Murumuru butter, Almond butter, Avocado butter, Aloe butter, Mango butter, Beeswax, Soy wax, Candelilla wax, Rice-bran wax, Coconut wax. The hydrophobic treatment may be water repellent applications, hydrophobic surfactants, such as silicone polymers or polyethers. Examples are Zelan™ R3 from Chemours Company and REPELLAN®T from Pulcra Chemicals.

The hydrophobic treatment may be used in an amount which increases as the percentage of cotton fibers that is present in the first layer increases. The range of the hydrophobic treatment may be from 0.1 $g/m^2$ up to 10 $g/m^2$, preferably from 0.5 $g/m^2$ to 4 $g/m^2$ basis weight. The first layer may for example have a basis weight of from 10 $g/m^2$ to 50 $g/m^2$, or from 15 $g/m^2$ to 40 $g/m^2$.

Second Layer 2

The laminate 30, 30' has a second layer 2 in a face to face relationship with the first layer 1, as described above. The second layer 2 may be any type of web conventionally used in the art. For example it may be a nonwoven web of natural fibers, synthetic fibers or a combination of natural and synthetic fibers.

The list of synthetic fibers and of natural fibers corresponds to the list disclosed above for the first layer of the topsheet. Typical the synthetic fibers are selected from the group consisting of polypropylene, polyethylene, polyester, polyethylene terephthalate, polybutylene terephthalate, polyamide, polylactic acid, and combinations thereof. The synthetic fibers may be single component fibers, multi-component fibers such as bicomponent fibers and combinations thereof. The fibers may have any suitable deniers or denier ranges and/or fiber lengths or fiber length ranges.

Several examples of nonwoven materials suitable for use as a second layer include, but are not limited to: spunbonded nonwovens; carded nonwovens; air through bonded carded nonwovens; spunlace nonwovens; needle punched nonwovens and nonwovens with relatively specific properties to be able to be readily deformed. The nonwoven web can be formed from many processes, such as, for example, air laying processes, wetlaid processes, meltblowing processes, spunbonding processes, needle punching processes and carding processes. The fibers in the nonwoven web can then be bonded via spunlacing processes, hydroentangling, calendar bonding, through-air bonding and resin bonding. The second layer may typically have a basis weight of from 5 $g/m^2$ to 50 $g/m^2$, or from 7 $g/m^2$ to 30 $g/m^2$, or from 7 $g/m^2$ to 20 $g/m^2$.

Apertures 5

Figure 7:
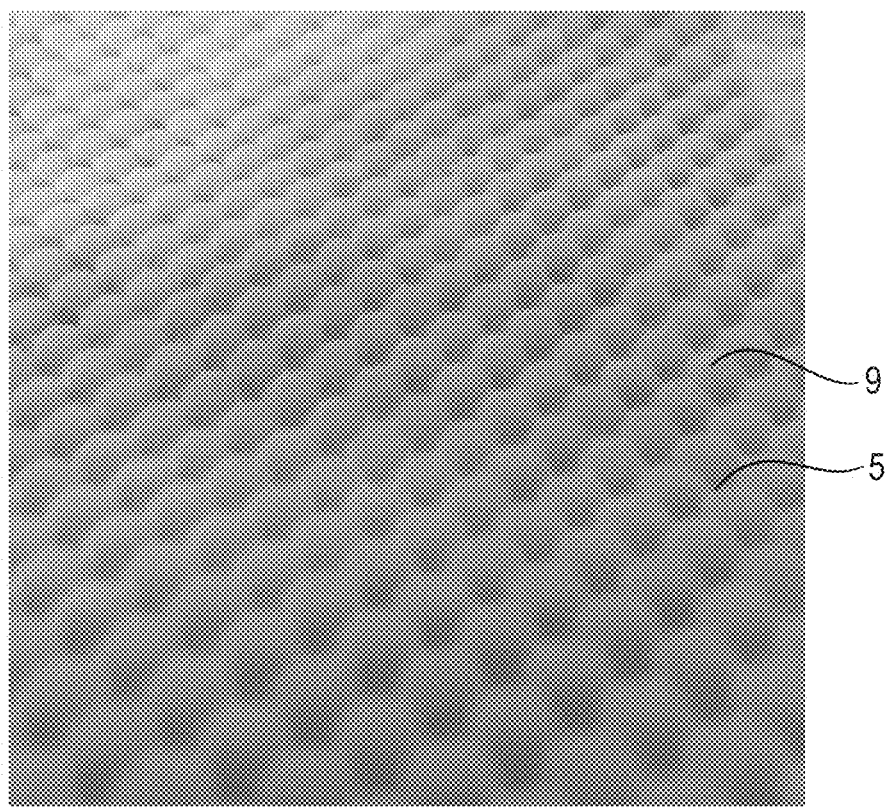
FIG. 7 is a photograph of an exemplary laminate according to the invention having protrusions and apertures.
Figure 8:
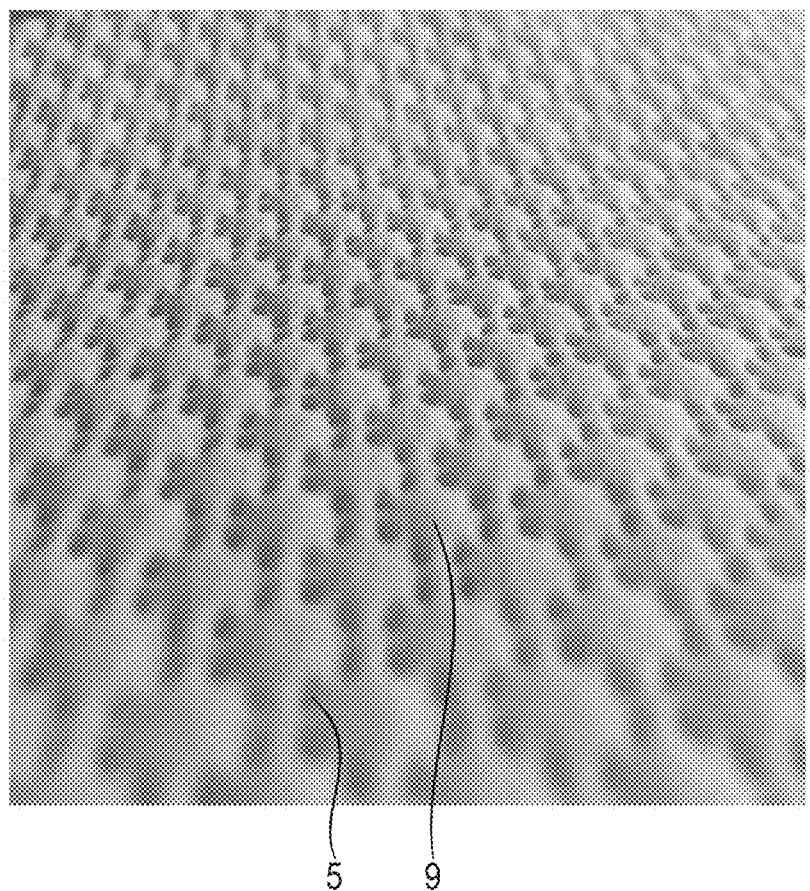
FIG. 8 is a photograph of an alternative exemplary laminate according to the invention having protrusions and apertures.

As illustrated in FIG. 1, the laminate 30 may comprise a plurality of apertures 5 extending through the first layer 1, advantageously also through the second layer 2, and thus typically through the whole thickness of the laminate 30. Apertures are particularly useful when the laminate 30 is used on the wearer-facing side as (part of the) topsheet 24. The apertures 5 may be typically regularly aligned according to a desired pattern, for example as shown in the pattern of FIG. 7 or FIG. 8.

The second layer 2 may have a plurality of apertures 5 at least partially, or completely aligned with the apertures 5 of the first layer 1. The apertures 5 of the first layer 1 and of the second layer 2 may thus be the same apertures. The plurality of apertures 5 of the second layer 2 may have at least partially the same width and/or length as the apertures 5 of the first layer 1.

The side walls of the apertures in the first layer 1 may be shorter than the side walls of the apertures in the second layer 2. Therefore, at the bottom part of the apertures 5, the apertures 5 may be only formed by the second layer 2. The first layer 1 may comprise land areas 8 between the majority of, or between all of the apertures 5. The land areas 8 may be substantially flat areas. Preferably, the land areas 8 are flat areas. The land areas 8 may fully surround the apertures 5. The land areas 8 may together form a generally continuous grid through the first layer, while the apertures 5 may be discrete elements throughout the first layer.

The second layer 2 may comprise land areas 12 between the majority of the apertures 5. The land areas 8 of the first layer 1 may be aligned with the land areas 12 of the second layer 2. The land areas 8 of the first layer 1 and the land areas 12 of the second layer 2 may fully surround the apertures 5 of the first layer 1 and of the second layer 2. The land areas 8 of the first layer 1 and the land areas 12 of the second layer 2 may be substantially flat areas. Preferably, the land areas 8 of the first layer 1 and the land areas 12 of the second layer 2 are flat areas.

The plurality of apertures 5 may be uniformly distributed on the first layer 1. To ensure material stability, the smallest distance between the majority of the apertures regardless of their particular shape and size is preferably at least 0.3 mm, preferably at least 1.0 mm. This distance is measured center-to-center on the first surface of the first layer of the topsheet.

The apertures 5 may extend inwardly, thus away from the wearer-facing side and toward the absorbent core when the laminate is disposed on the wearer-facing side of the article. The side walls of the apertures of the first layer and of the second layer may extend at least 0.1 mm beyond the first surface of the first layer, preferably at least 0.2 mm beyond the first surface of the first layer. The apertures may be tapered and take a conical shape such that the diameter of the aperture is larger proximate the second surface than the diameter of the opening proximate the bottom edge of the aperture. The apertures may vary in shape. For example, the shape of the apertures as seen from the first surface of the first layer may be circular, elliptic, rectangular or polygonal. Preferably, the apertures have a circular shape, an elliptic shape or a polygonal shape. The tridimensional shape of the apertures may be cylindrical (e.g. with a circular or elliptic base), prismatic (e.g. with a polygonal base), truncated cone or pyramidal. Though less preferred, the plurality of apertures of the first layer and of the second layer may be simply holes with no side walls.

Topsheets with apertures generally have an increased risk of rewet, i.e. of liquid passing back components underneath the topsheet (such as the absorbent core) into and through the topsheet. For apertured hydrophobic topsheets (for the present invention: when the first layer is hydrophobic), rewet occurs predominantly through the apertures. The tapered shape of the apertures can help to reduce rewet, as the diameter of the apertures toward the absorbent core is smaller than the diameter of the aperture in the first layer. Moreover, if the first layer is hydrophobic, the side walls of the apertures of the hydrophobic first layer overlay the side walls of the second layer (which may be hydrophilic), thus further reducing the risk of liquid passing back through the apertures.

The apertures may also vary in size. Smaller apertures can contribute to lower rewet and generally tend to create less red marking on the skin of the wearer. Hence, the apertures may have a size of 4 mm$^2$ or less, of 3.5 mm$^2$ or less, of 3.0 mm$^2$ or less, or of 2.5 mm$^2$ or less. The size of the apertures may not be less than 0.2 mm$^2$, advantageously not less than 0.5 mm$^2$. The size is determined on the surface of the laminate which is most outwardly placed, so typically the first side of the first layer, and e.g. for conical apertures the larger aperture opening is determined.

Especially, when the first layer comprising a relatively high amount of natural fibers, bonding the first and second layer to each other using heat may be difficult. As the natural fibers do not become tacky or melt upon exposure to heat, the first layer may not properly and durably bond to the second layer. The first layer is thus attached to the second layer in bonding areas by hot-melt adhesive, which will be discussed in more details in a dedicated section below. The bonding areas may be at the land areas 8, 12 and/or at the apertures 5.

Hot-Melt Adhesive

The first layer 1 and the second layer 2 forming the laminate 30, 30' are intermittently bonded to each other by a hot-melt adhesive (the adhesive layer is not represented in the Figures). The hot-melt adhesive bonding advantageously provide a strong enough bond between the first and second layer to reduce the risk of delamination during use, especially when the laminate is used as topsheet and has been wetted. This was found to be a challenge for natural fibers. The hot-melt adhesive should also be safe to use, as it may be in contact with the skin of the wearer of the absorbent article via the apertures.

The hot-melt adhesive of the invention comprises as main ingredient a heterophase polymer. "Heterophase" polymer refers herein to a polymer having an amorphous character and at least some substantial crystalline content that can provide cohesive strength in the cooled adhesive mass. The crystalline content can be in the form of stereoregular blocks or sequences. The heterophase polymer is advantageously a single material, but it may also be a blend of two or more heterophase polymers having the required properties. Heterophase polymers are typically co-polymers, that is polymers formed by the polymerization of at least two different monomers. Homopolymers on the other hand are polymers resulting from the polymerization of a single monomer, i.e., a polymer consisting essentially of a single type of repeating unit. The hot-melt adhesive may in particular comprise more than 90% by weight of the adhesive of such a heterophase polymer.

While not wishing to be bound by theory, it is believed that the hot-melt adhesive of the invention, comprising as main ingredient a heterophase polymer, is able to form good bonds with natural fibers such as cotton, and the bonds are maintained even under in-use conditions. When the cotton fibers soak water, the Van der Waals adhesion forces at the interface between the wet fibers and a conventional hot-melt adhesive are disrupted and the bond can easily open. The heterophase polymers of the invention, however, are able to create a strong mechanical lock via the geometric effect of fiber entanglement in combination with a high cohesive strength provided by its crystalline character. This enables to create strong bonds even if the fibers are not "perfectly" entangled (by 360° entanglement angle), but only partially entangled (e.g. up to 180°). A non-perfect entanglement is particularly observed when hot-melt adhesive are applied at a relatively low adhesive basis weight (below 10 g/m$^2$). With a conventional adhesive, significantly higher basis weights are required (ensuring 360° fiber entanglement on every local bond point) in order to compensate for the lower cohesive strength.

It was found that suitable heterophase polymers have an enthalpy of fusion of at least 10 J/g, as measured according to the Enthalpy of Fusion Measurement Method described below. The enthalpy of fusion is useful to characterize the crystallinity of heterophase polymers and is indicative of the level of crystallinity of the polymer. Put simply, the higher the enthalpy of fusion is, the more crystalline character the polymer has. Amorphous polymers such as styrene block copolymers (SBS, SIS, SEBS, SEPS) have no or little enthalpy of fusion.

The enthalpy of fusion of the heterophase polymer may in particular be at least 15 J/g and up to 40 J/g, which is representative of moderately crystalline polymers. By comparison, amorphous polymers have no significant enthalpy of fusion. Styrene block copolymers (SBC) like SBS, SIS, SEBS, SEPS can have some (low) crystallinity but typically below 10 J/g. The hot-melt adhesives of the invention may thus be typically free of Styrene Block Copolymers.

Having a polymer with an enthalpy of fusion that is too high may on the other hand equate with a bond that is too brittle, e.g. Licocene® 6502 with 82.1 J/g. The enthalpy of fusion of the polymer may thus advantageously range from 15 J/g to 40 J/g, more particularly from 20 J/g to 35 J/g.

While not wishing to be bound by a particular type of chemistry, copolymers of at least two different monomers selected from propylene, ethylene, and/or other olefins selected from the group of higher alpha olefins with 4 to 20 carbon atoms, may be used in the invention. The copolymer may be produced using metallocene catalysts, as is known in the art. The heterophase polymer may be in particular a propylene-ethylene copolymer. The content of ethylene derived units may be lower than 30% (molar %.). Nonlimiting examples of such copolymers are commercially available in the Licocene® series from Clariant. Licocenes® comprise C3/C2 copolymers of mid molecular weight, produced by using metallocene catalysts. The molar propylene content is typically larger than 70%. Such co-polymers have a glass transition temperatures below −10° C.

Example of suitable propylene-ethylene copolymers from Clariant are Licocene® PP 1502 which has a measured enthalpy of fusion of 15.1 J/g, Licocene® PP 1602 which has a measured enthalpy of fusion of 16.7 J/g, or Licocene® PP 2502 which has a measured enthalpy of fusion of 29.4 J/g.

It was also found advantageous that the adhesive should be sufficiently solidified and non-tacky at temperatures typically occurring in use and during storage of the article. Otherwise, when the absorbent article is compressed, there is a risk that the protrusions 9 in the first layer 1 collapse and bond to the second layer 2, thus impairing the protrusions from keeping their empty volume 14. Compression will typically occur when the articles are within the package after manufacturing prior to opening by the consumer, and when a wearer imparts pressure (e.g. by sitting) during use.

Another advantage of a non-tacky adhesive under in-use conditions is to exclude that the adhesive sticks to the baby's skin in case some of the adhesive would bleed through the apertures of the laminate or though thin spots (low local basis weight) of the substrate directed to the baby's skin (first layer). While the process is normally optimized in a way that such bleed-through of adhesive be prevented, a non-tacky adhesive will enable a generally broader process window, which is beneficial for line speed increase, or the usage of thinner and less expensive first layer materials. If bleedthrough should in such case involuntarily happen, even at a low extent, it will not render the outward-facing surface of the first layer tacky.

Accordingly, to address these problems, the hot-melt adhesive may advantageously have a storage modulus (G') that is higher than $0.3 \times 10^6$ Pa at 37° C., as measured with the Oscillatory Rheometry Test Method described below. The relative high G' value is indicative of an adhesive that is not tacky during use. The hot-melt adhesive may in particular have a storage modulus (G') higher than $1.0 \times 10^7$ Pa at 37° C., or even $1.5 \times 10^7$ Pa at 37° C. On the other hand, the hot-melt adhesive may also have a storage modulus (G') that is lower than $2.0 \times 10^8$ Pa at 37° C.

The G' value of polymers typically decreases with the temperature. The hot-melt adhesive may have a storage modulus (G') higher than $0.3 \times 10^6$ Pa at 23° C., or even $1.5 \times 10^7$ Pa at 23° C., or even $2.0 \times 10^7$ Pa at 23° C. On the other hand, the hot-melt adhesive may also have a storage modulus (G') that is lower than $3.0 \times 10^8$ Pa at 23° C.

The hot-melt adhesive may preferably also have a storage modulus (G') higher than $0.3 \times 10^6$ at 60° C. (reflecting storage conditions in countries with hot climate, as e.g. measured in containers). The hot-melt adhesive may also have a storage modulus (G') higher than $0.3 \times 10^6$ at 70° C., as indicative of the temperature which the hot-melt has in the process (after initial cool-down due to heat exchange with the substrate onto which it has been applied) when it gets into contact with aperturing tooling. A non-tacky behavior in the temperature range of about 40° C. to about 70° C. contributes to avoid contamination of the tooling, which can lead to frequent line stops.

Commercially available propylene-ethylene copolymers such as those from Clariant's Licocene have the following G', as measured as indicated below: Licocene® PP 1502 has a G' value of $1.4 \times 10^7$ Pa at 23° C. and $1.0 \times 10^7$ at 37° C., Licocene® PP 1602 has a G' value of $1.2 \times 10^7$ at 23° C. and $8.6 \times 10^6$ at 37° C., Licocene® PP 2502 has a G' value of $5.2 \times 10^7$ at 23° C. and $3.3 \times 10^7$ at 37° C.

For processability reason, the heterophase copolymer may advantageously have a viscosity of less than 20,000 mPa·s (1 centipoise [cps]=1 mPa·s), for example less than 15,000 mPa·s, or less than 10,000 mPa·s or even less than 5,000 mPa·s, when measured at 190° C. using a Brookfield viscometer (as measured by ASTM D 3236), which is also referred to herein as "viscosity" and/or "Brookfield viscosity". A lower viscosity at these temperatures enables spraying of the hot-melt adhesive. Licocene® 2502 for example has a viscosity of about 3.400 mPa·s at a spray application temperature of 150° C.

Figure 3:
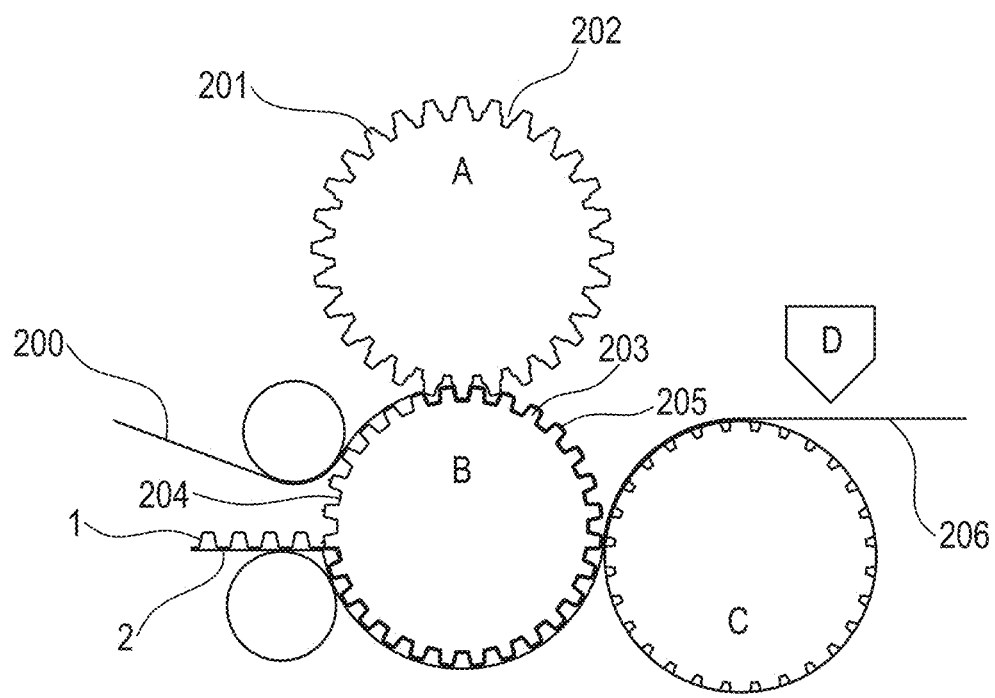
FIG. 3 is a schematic illustration of a process for making a laminate as in FIG. 1.

The hot-melt adhesive may be applied using conventional application method, in particular non-contact method such as spraying which creates a discontinuous adhesive pattern (e.g. random, or spiral) and which uses less adhesive than contact-method such as extrusion, slot or roll-coating. The hot-melt adhesive may be typically applied to the whole of the first surface 10 of the second layer 2, in particular the hot-melt adhesive may be sprayed on this surface, so that the hot-melt adhesive is present not only in the area of attachments in the land regions 8 and/or apertures 5 but also in the areas of the second corresponding to the protrusions 9. Before the hot-melt solidifies, the complementary layer (typically the first layer) can then be pressed in the selected areas where bonding between the first and second layers is desired (land areas 8 of the first layer and/or apertures 5), with the first layer having more material than the second layer so that the protrusions are formed in the first layer. Applying pressure in the bond areas is necessary for achieving sufficient bond strengths. Presumably this is due to the rapid solidification of the hot-melt adhesives of the present invention which requires the additional help of pressure to ensure penetration into the second substrate. The rapid solidification is believed to be due to the crystalline portion of the heterophase polymer. In the processes as illustrated in FIG. 3, the required pressure may be provided at the same time as the apertures are formed in the laminate first layer and second layer.

The hot-melt adhesive composition may advantageously comprise a single heterophase polymer (or possibly a mix of heterophase polymer having the required properties) and no amorphous polymers. The hot-melt adhesive may in particular comprise at least 90% by weight, or at least 95%, or even at least 98% or 99% by weight of the adhesive of the heterophase polymer(s). Accordingly, the adhesive composition may comprise less than 10 wt. %, alternatively less than 5 wt. %, alternatively less than 3 wt. %, alternatively less than 2 wt. %, alternatively less than 1 wt. % of additives. Typical additives that may be used in the hot-melt composition include plasticizers (including plasticizing oils or extender oils) that can reduce the viscosity in the adhesive composition, antioxidants and stabilizers, in particular UV stabilizer that may prevent or reduce the degradation of the composition by radiation, brighteners, colorants (including pigments), fragrances such as a perfume or other odorant, and fillers. Examples of such additives are described in more details e.g. in WO2015/191802A1 (Bunelle et al., P&G). The adhesive may in particular consist of the heterophase polymer and such additives. The hot-melt adhesive may also be free of styrenic block copolymers (SBC).

The hot-melt adhesive composition is preferably free of tackifiers used in conventional adhesives that are tacky in the temperature range of 0° C. and 40° C. Common tackifiers are C5 resins, petroleum distillates, hydrogenated hydrocarbons, C5/C9 resins, C9 resins, polyterpenes, rosins, hydrogenated rosins, rosin esters and mixtures thereof.

Moreover, the hot-melt adhesive may have a softening point of more than 60° C., preferably more than 80° C., more preferably more than 90° C. according to the ASTM E28-99 test method. If the hot-melt adhesive becomes soft below a temperature of 60° C., the hot-melt adhesive becomes typically tacky at room temperature (25° C.) and at atmospheric pressure (760 mmHg; i.e. $1.013 \times 10^5$ Pa) or at body temperature (37° C.) during use of the absorbent article.

As indicated previously, the hot-melt adhesive may typically be applied at a basis weight of at least 1 g/m$^2$, or at least 2 g/m$^2$, or at least 3 g/m$^2$ and up to 15 g/m$^2$, or up to 10 g/m$^2$, for example at 5 g/m$^2$, with a preferred method of application being spraying the molten hot-melt adhesive on the first side 10 of the second layer 2, and then immediately bonding the first layer to this second layer while the adhesive still retains sufficient tack to make the bonds.

Method of Making the Laminate 30 of the Invention

The three-dimensional laminate (with or without apertures) may be industrially produced at high speed by any known and suitable methods, for example as described in WO2017/156200 (Orr et al., P&G) and PCT application CN2018/110397, filed Oct. 16, 2018 (Erdem et al, P&G). FIG. 3 is a schematic illustration of one example process for forming protrusions in the first layer and bonding this layer to a second layer, which is briefly discussed below. More details of this process, including photographs of the embossing rolls, can be found in PCT application CN2018/110397.

Referring to FIG. 3, a first substrate 200 may go through a pair of rolls named A and B. The first substrate may comprise natural fibers such as cotton in order to form the first layer 1 of the laminate. The speed of the roll A and B may be from 5 to 600 meters/minute. The temperature range of the roll A may be from 40° C. to 200° C. The temperature range of the roll B may be from 30° C. to 200° C. The roll A may comprise a plurality of protrusions 201 extending radially outwardly from the roll A. The roll A may also comprise a plurality of recesses 202 formed in a radial outer surface of the roll A. The depth of the recesses 202 of the roll A may be from 0.5 to 10 mm, the height of the protrusions 201 of the roll A may be from 0.5 to 9 mm. The roll B may comprise a plurality of protrusions 203 extending radially outwardly from the roll B. The roll B may also comprise a plurality of recesses 204 formed in a radial outer surface of the roll B. The distal end of the plurality of protrusions 203 of the roll B may have the shape of a pin 205.

The protrusions 201 on the roll A may have a different size, shape, height, area, width and/or dimension than the protrusions 203 on the roll B. The recesses 202 formed in the roll A may have a different size, shape, height, area, width, and/or dimension than the recesses 204 formed in the roll B. The recesses 202 in the roll A may be configured to at least partially receive the protrusions 203 of the roll B, thereby creating the protrusions in the first substrate 200. The roll A may comprise a plurality of holes in the recesses area in order to receive the shape of pin 205 of the protrusions 203 of the roll B. Therefore, a plurality of apertures 5 are formed in the first substrate 200 between each two adjacent protrusions of the first substrate 200. The first substrate 200, after going through the roll A and the roll B may comprise a plurality of protrusions 9 and a plurality of apertures 5 between each two adjacent protrusions.

A second substrate 206 may be brought by a concave roller C. The hot-melt adhesive can be added on the first surface of the second substrate 206 by an equipment D before the second substrate 206 is in contact with the first substrate 200. The hot-melt adhesive can be advantageously uniformly sprayed on the second substrate at the basis weight indicated previously, for example 5 g/m². The roll C may comprise a plurality of holes in order to receive the shape of pin 205 of the protrusions 203 of the roll B. The second substrate 206 may pass through the roll C and the roll B and contact with the first substrate 200 at the protrusions 203 of the roll B. As the protrusions 203 of the roll B may have the shape of a pin, a plurality of apertures may be created also on the second substrate 206. The apertures in the second substrate 206 may in this way be aligned with the apertures in the first substrate 200. Pressure is applied in the land areas of the first layer and the second layer so that the adhesive forms bonds between the first and second layers to form the laminate. At the end of this process, a laminate material as illustrated in FIG. 1 comprising a three-dimensional, apertured first layer 1 in contact with a second layer 2 between the protrusions 9 of the first layer is obtained.

(Partial) penetration of the fibers of the first layer into the second layer at the apertures improves the integrity of the topsheet by reducing the risk of delamination of the first and second layer. Fiber penetration creates "anchor points" which stabilizes the laminate of first and second layer, even if the contact area between first and second layer is reduced as only the first layer has protrusions. The anchor points also reduce the risk of fiber fuzzing.

A laminate 30' according to the invention but without apertures, as for example illustrated in FIG. 2, may be more easily made by first forming a three-dimensional first layer, typically by engaging a first substrate material between a first and second forming members and mechanically deforming the substrate to form a first layer having a three-dimensional shape. Such methods are well known, and for example are described in WO2017/156200 and WO2017/156203, and PCT application CN2018/110397. The adhesive is then applied, e.g. by spraying, on the second substrate and the first layer is bonded to the second substrate by applying pressure in the land areas 8, but without aperturing, to form the dual layer laminate of the invention.

In addition to using adhesive, the first layer may be attached to the second layer in the bonding areas by embossing or by pin bonding. The term "embossing" means creating bonding points between the first layer and the second layer by heat or pressure for example.

Absorbent Article 20

Figure 4:
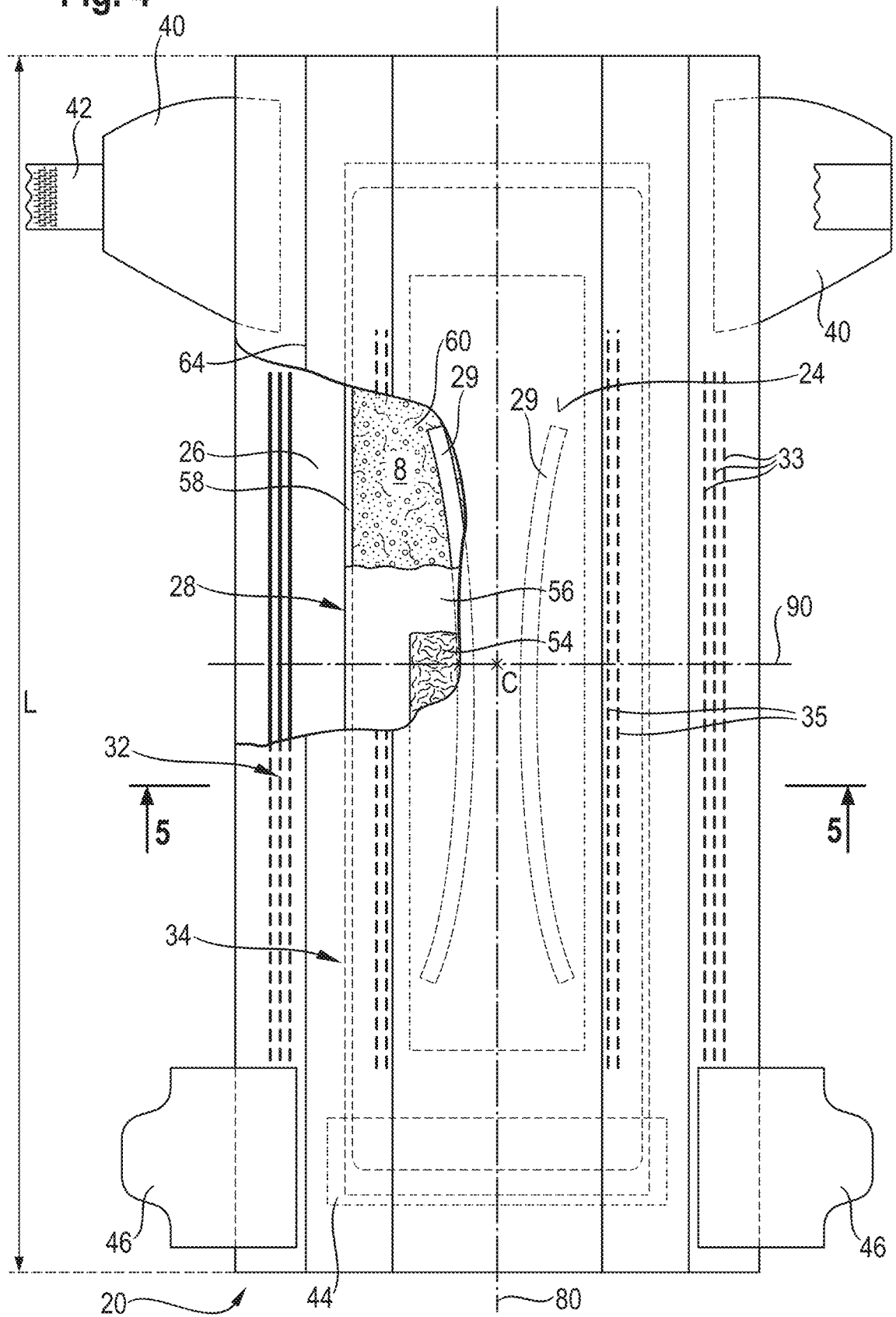
FIG. 4 is a schematic view of an exemplary taped diaper that may incorporate a laminate according to the invention.
Figure 5:
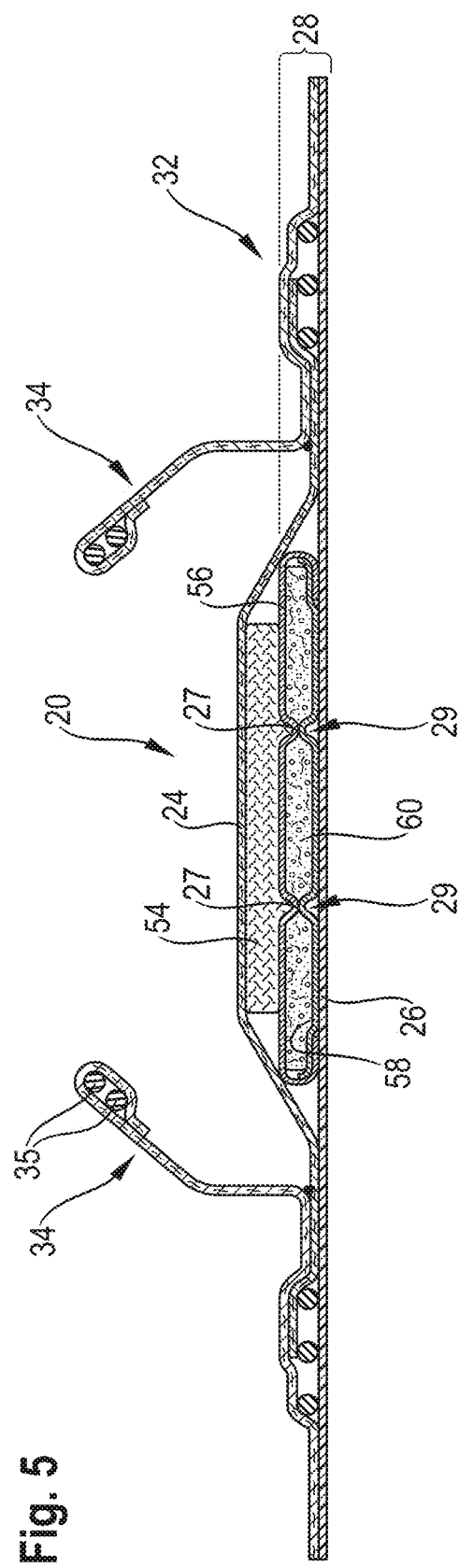
FIG. 5 is a schematic transversal cross-section of the diaper of FIG. 4.
Figure 6:
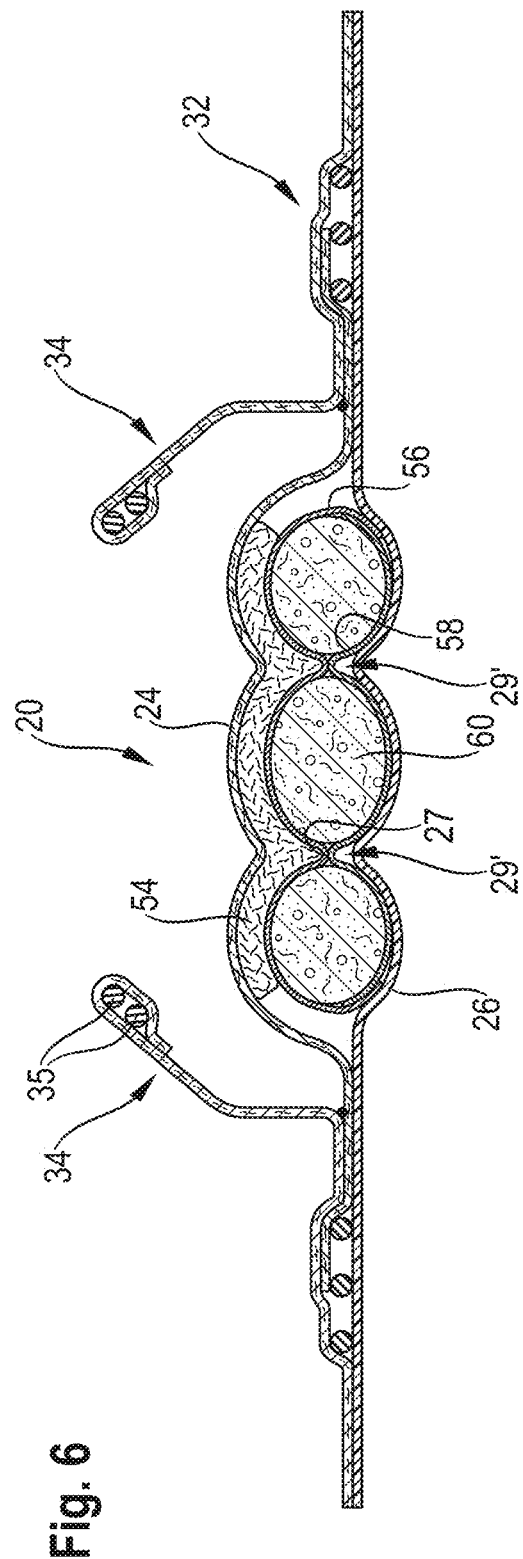
FIG. 6 is a schematic cross-sectional view of the diaper of FIG. 4 with the core having absorbed a fluid and swollen.

The absorbent articles may be any conventional absorbent articles as listed previously, such as taped or pant diapers. An exemplary taped diaper 20 is represented in FIGS. 4-6. This diaper is shown for illustration purpose only as the present invention is applicable to a wide variety of diapers or other absorbent articles. The absorbent article 20 notionally comprises a longitudinally centerline 80 dividing the article in a left side and a right side, and a perpendicular transversal centerline 90 disposed at half the length of the article as measured on the longitudinal centerline 80, with both centerlines crossing at the center point C.

Typical diapers components include, from top to bottom, the topsheet 24, an acquisition layer (or system) 54, an absorbent core 28 and the backsheet 26. Inner and outer lateral barrier cuffs 34, 32, which are preferably elasticized with elastic strands 35, 33 respectively are typically present. The acquisition system may comprise a single layer (typically an hydrophilic air-through bonded carded nonwoven) or two or more layers as is known in the art. Elasticized back ears 40 having a tape end 42 can be attached to a landing zone 44 at the front of the article. Front ears 46 are typically present in such taped diapers to improve containment and attachment.

The absorbent core 28 can absorb and contain liquid received by the absorbent article and comprise an absorbent material 60, which may be a blend of superabsorbent polymer particles and cellulose fibers or pure superabsorbent polymer particles, for example immobilized by a net of glue as is known in the art. The absorbent core 28 may comprise absorbent material free channels 29, through which the top side 56 of the core wrap may be bonded to the bottom side 58 of the core wrap. The core wrap bonds 27 may at least persist as the absorbent core 28 swells upon liquid absorption and creates three-dimensional channels at the wearer-facing surface of the article, as illustrated in FIG. 6. Of course, this is entirely optional, the absorbent core may also not have bonded channels, or even unbonded channels. The absorbent material defines an absorbent material area 8, which may be rectangular as show in in FIG. 4, but it is also common to have a shaped area which is tapered in the area around the transverse centerline 90. The patent literature is replete with example of such and other components suitable for use in the diapers of the invention, see for example already referred to WO2017/156200 (Orr et al. P&G) and PCT application CN2018/110397 filed Oct. 16, 2018 (Erdem et al, P&G), and these will not be discussed in extension herein.

The three-dimensional laminate 30 of the invention may be disposed on the wearer-facing side or the garment-facing side of the article. For example, the topsheet 24 may be partially or entirely formed by a three-dimensional laminate according to the invention. The topsheet 24 is not represented in a three-dimensional form in the FIGS. 4-6 for simplification. The topsheet 24 may alternatively be a multi-component topsheet as for example disclosed WO2015/134371A1 and WO2015134375 (both Tally et al., P&G) with the three-dimensional laminate of the invention extending longitudinally along the longitudinal centerline 80, and with the lateral side portions of the topsheet being formed by a simpler, flat nonwoven. The laminate of the invention may also be attached to a conventional topsheet layer The wearer-facing side of the article may comprise a single type of topsheet material, but it is also envisaged that the topsheet comprises different materials for different areas of the wearer-facing surface (multi-components topsheet). Such multi-component topsheets may for example comprise a laminate topsheet 30 according to the present invention disposed centrally on the wearer-facing side of the article, and another topsheet material (typically less costly) at the lateral sides of the wearer-facing side for the rest of topsheet. Such multi-component topsheets are for example disclosed WO2015/134371A1 and WO2015134375 (both Tally et al., P&G).

The three-dimensional laminate may also be disposed on the garment-facing side of the article. Conventional backsheet comprise a liquid impermeable polymer film, which is optionally externally doubled by a low basis weight flat nonwoven outer cover ("NWOC") to improve the feel of the garment-facing side of the article. The laminate 30 of the invention may be used to replace this outer cover, thus providing a three-dimensional soft pattern on the backsheet side of the article.

The first layer may also be oriented outwardly relative to the article, so that the protrusions can be felt by the caretaker or a user feeling the garment-facing side of the article. The material used for the first layer and second layer may be as disclosed above, in particular soft natural fibers may be present in the first layer, which is oriented outwardly, as previously discussed. The first layer may in particular be a spunlace layer (with or without natural fibers) and the second layer may be another spunlace, or a carded airthrough bonded or a spunbond nonwoven. The first layer and second layer may be both hydrophobic, or only one of these layers. Alternatively the second layer may be a polymeric film as is commonly used in backsheet. Typically, conventional backsheet comprises such a polymer film, which may be breathable or not, but is liquid impermeable. The three-dimensional laminate 30, 30' may thus comprise as second layer such a polymeric film, and as first layer an outwardly laying layer of spunlace or another nonwoven, with or without natural fibers.

Of course the articles of the invention may comprise a first laminate as described herein on the wearer-facing side and a second laminate on the garment-facing side. Both laminates may be the same, but they may also be different, as suggested before the laminate on the wearer-facing side may advantageously comprise apertures while the laminate on the garment-facing side may not require such apertures.

Test Methods

Peel Force Measurement Method:

The Peel Force Measurement Method is used to determine the Peel Force between the first layer and the second layer of a laminate material as described herein. The laminate specimen required is 150.0±0.1 mm in length and 50.8±0.1 mm (2 in.) wide. A laminate sample can be removed from an absorbent article. The sample is taken at the intersection of the longitudinal and lateral centerlines of the absorbent article, with the 50.8 mm wide dimension being oriented along the lateral width of the absorbent article. For the purpose of removing the laminate (typically as part of the topsheet 24 or backsheet 26) from the absorbent article, a razor blade is used to excise the laminate from the underlying layers of the absorbent article around the outer perimeter of the 150.0 mm×50.8 mm area. A cryogenic spray (such as Cyto-Freeze, Control Company, Houston TX) can be used to remove the specimen from the underlying layers, if necessary. If the dimensions of the absorbent article do not allow to excise an area of 50.8 mm×150 mm, then the largest possible rectangular topsheet area will be excised from the absorbent article with the procedure above. Prepare 4 more specimens in like fashion.

The laminate specimens are analyzed according to the National Standard of People's Republic of China standard method GB 8808-88, with the following specific choices and modifications: Testing speed Method A is used in which the crosshead speed is 300 mm/min; the specimens used are 50.8±0.03 mm in wide and 150.0±0.1 mm long; and specimens are oriented in the tensile tester with the dimension of the specimen that was (or would be in a finished article) parallel to the longitudinal axis of the article being oriented parallel to the direction of crosshead travel.

The average peel force values such measured is determined according to GB 8808-88 and is defined as the Peel Force and is reported to the nearest 0.01 N/(50.8 mm).

The Peel Force may also be measured after conditioning the specimens under specified conditions. For measuring the Wet Peel Force, the specimens are completed soaked in demineralized water without folding and kept under water for 12 hours at 21° C. They are taken out of water and tested same as the dry samples. The Wet Peel Force may be compared to the Dry Peel Force, which is measured on equivalent specimens that have not been contacted by a fluid.

For measuring the Aged Peel Force, the specimens are kept 4 weeks at 40° C. at 50% relative humidity ("Aged" values). The Aged Peel Force can be compared to the Fresh Peel Force, which is measured on equivalent specimens kept 3 days at 21° C. and 50% relative humidity ("Fresh" value).

Enthalpy of Fusion Measurement Method

The Enthalpy of Fusion of a hot-melt adhesive composition is determined using the Enthalpy of Fusion Test Method, which consists of performing ASTM D3418-15 with the following additional guidance. Hot-melt specimen(s) are preferably extracted from molded or pelleted raw material adhesive composition. If raw material is not available, specimen(s) of adhesive are extracted from bonds of interest in an absorbent article using techniques known to those of skill in the art. Dry nitrogen is used as the purge gas in the differential scanning calorimeter (DSC). The rate of increase of temperature in the DSC is 10° C./min, and the rate of decrease of temperature in the DSC is 1° C./min. The mass-normalized enthalpy of fusion is calculated as specified in section 11.4 based on the curve corresponding to decreasing temperature (at 1° C./min) and is reported as the "Enthalpy of Fusion" in units of joules per gram (J/g) to the nearest 0.1 J/g.

Oscillatory Rheometry Test Method

The Oscillatory Rheometry Test Method is used to measure the Storage Modulus (G') and the Loss Factor of a hot-melt adhesive composition. A controlled-stress rotational rheometer (such as Discovery HR-3, TA Instruments, New Castle, DE, USA, or equivalent) capable of sample temperature control (using a Peltier cooler and resistance heater combination) with a precision equal to or exceeding 0.5° C. over at least the range of −10° C. to 150° C. The rheometer is operated in a parallel plate configuration with 20-mm stainless steel parallel-plate tooling.

A parallel plate gap of 1000 µm is initially used in the method. To compensate for thermal expansion of the tooling, the gap is set to 1000 µm, and a mapping of actual plate gap (as measured using a suitable standard test fluid) a function of temperature over the range −10° C. to 150° C. is performed. This mapping is then used throughout the determination of the Storage Modulus Parameter and the Loss Factor Parameter.

The rheometer is heated to 150° C., hot melt adhesive composition is introduced in the rheometer, the gap is set to 1050 µm, excess protruding sample is trimmed, and the gap is then set to 1000 µm. The axial force control of the rheometer is set to be maintained within ±0.1 N of force, and the thermal expansion/contraction of the sample itself is compensated in order to avoid overfilling or underfilling of the gap in addition to the abovementioned compensation of the tooling. The rheometer is then allowed to cool to 130° C., at which point the measurement commences with temperature ramped from 130° C. to −10° C. at a constant rate of cooling of 2° C./min. The applied strain amplitude is 0.1%, and the frequency of oscillation is 1 Hz (that is, one cycle per second). The resulting oscillatory stress is recorded.

After this step, the sample temperature is set to 23° C. (temperature is ramped to this setpoint at a rate of 10° C./min), and the sample is allowed to rest for 4.0 hours at 23° C. At the end of this period, the temperature is set to −10° C. (temperature is ramped to this setpoint at a rate of 10° C./min), the sample is equilibrated for 300 seconds at −10° C., and a second oscillatory rheology measurement is conducted (0.1% strain, frequency of oscillation of 1 Hz) while temperature is ramped upward to 130° C. at a constant rate of increase of 2° C./min.

From the second, increasing temperature sweep, the storage modulus G' is calculated and recorded at 23° C. and 37° C., and these values are reported in megapascals (MPa) to the nearest 0.01 MPa as the "Storage Modulus at 23° C." and the "Storage Modulus at 37° C.," respectively. The G' values may also be measured at other temperatures, as is known in the art. From the second, increasing temperature sweep, the loss factor (also known as tan delta) is calculated recorded at 23° C. and 37° C., and these dimensionless values are reported to the nearest hundredth as the "Loss Factor at 23° C." and the "Loss Factor at 37° C.," respectively.

EXAMPLES

Examples of Three-Dimensional Laminate, that May be Used as Topsheet

In the examples 1-22 below, the first layer was a 35 gsm (g/m$^2$) 100% cotton fibers spunlace nonwoven that had been hydrophobically treated. The second layer was an air-through bonded carded web made of PE/PET sheath/core bicomponent fibers, tested at different basis weight, namely 22 g/m$^2$ (Z73-22), 24 g/m$^2$ (Z02-24) and 40 g/m$^2$ (Z85B-40), all ex. Xiamen Yanjan New Material Co. Ltd, Xiamen City.

The first and second layers were processed as illustrated in FIG. 3 to obtain an apertured three-dimensional nonwoven as illustrated in FIG. 1 with the pattern of FIG. 8. These examples may be in particular disposed on the wearer-facing side of an absorbent article, i.e. as part of a topsheet.

The amount and nature of the hot-melt adhesive was varied between the examples as described below. In the inventive examples, the inventive hot-melt adhesive was Licocene® PP 2205 TP ex. Clariant ("inv"), and the comparative adhesive a conventional tackifier-containing construction adhesive (DM5813U ex. Henkel, "comp"). The adhesive used was sprayed at different basis weight: 3 gsm, 4 gsm and 5 gsm. The temperature of the tank, pipe and spray gun was also recorded. For simplicity, the Peel Forces below were measured on the laminates as component without having first been assembled into an article.

Peel Force Dry and Peel Force Wet Comparison

In this set of data, the Peel Force was measured for different laminates and were compared in dry state and wet state (after soaked in demineralized water for 12 hours). For each specimen, the first layer and the second layer forming the topsheet are peeled off, according to the Peel Force Method described above.

| Example # | Adhesive basis weight | Adhesive application temp, in ° C. (tank/pipe/gun) | Second layer | Dry Peel Force | Wet Peel Force | Dry/Wet Peel Force Difference (%) |
| --- | --- | --- | --- | --- | --- | --- |
| 1 (inv) | 3 gsm | 130/135/140 | Z73-22 | 0.65 | 0.44 | −32% |
| 2 (inv) | 4 gsm | 130/135/140 | Z73-22 | 0.77 | 0.78 | 1% |
| 3 (inv) | 5 gsm | 130/135/140 | Z73-22 | 1.26 | 0.98 | −22% |
| 4 (inv) | 3 gsm | 150/155/160 | Z73-22 | 0.33 | 0.38 | 15% |
| 5 (inv) | 4 gsm | 150/155/160 | Z73-22 | 0.44 | 0.47 | 7% |
| 6 (inv) | 5 gsm | 150/155/160 | Z73-22 | 0.91 | 0.52 | −43% |
| 7 (inv) | 3 gsm | 170/175/180 | Z73-22 | 0.35 | 0.23 | −34% |
| 8 (inv) | 4 gsm | 170/175/180 | Z73-22 | 0.36 | 0.19 | −47% |
| 9 (inv) | 5 gsm | 170/175/180 | Z73-22 | 0.74 | 0.70 | −5% |
| 10 (comp) | 4 gsm | 160/170/180 | Z73-22 | 1.47 | 0.53 | −64% |

The Dry/Wet Peel Force Difference is calculated from the measured values:
Dry/Wet Peel Force Difference = (Wet Peel Force − Dry Peel Force)/Dry Peel Force.

A negative value indicates a loss of Peel Force upon wetting. The Peel Force Loss for the comparative example (−64%) is significantly higher than for all the examples according to the invention. It is thus believed that the invention can help reducing the occurrence of unwanted delamination of the topsheet laminate during use. In addition, the tackifier-free adhesive of the invention prevents the first layer and second layer from becoming accidentally bonded in the protrusions.

The laminates of the invention may advantageously have a Dry/Wet Peel Force Loss of less than 50%, as measured according to the Peel Force Measurement Method described herein.

Fresh vs. Aged Peel Force Comparison

In this set of data, the Peel Force was measured for different laminates after 3 days at 21° C. and 50% relative humidity ("Fresh" value) and after 4 weeks at 40° C. at 50% relative humidity ("Aged" values). Different adhesive application temperatures were tested to compare the results based on modifying these conditions. For each specimen, the first layer and the second layer forming the laminate were peeled off according to the Peel Force Measurement Method described above.

| Example # | Adhesive basis weight | Adhesive application temp, in ° C. (tank/pipe/gun) | Second layer | Fresh Peel Force | Aged Peel Force | Fresh/Aged Peel Force Difference (%) |
|---|---|---|---|---|---|---|
| 11 (inv) | 3 gsm | 130/135/140 | Z73-22 | 0.65 | 0.40 | −37% |
| 12 (inv) | 4 gsm | 130/135/140 | Z73-22 | 0.77 | 0.79 | 3% |
| 13 (inv) | 5 gsm | 130/135/140 | Z73-22 | 1.26 | 1.05 | −16% |
| 14 (inv) | 3 gsm | 150/155/160 | Z73-22 | 0.33 | 0.26 | −19% |
| 15 (inv) | 4 gsm | 150/155/160 | Z73-22 | 0.44 | 0.69 | 56% |
| 16 (inv) | 5 gsm | 150/155/160 | Z73-22 | 0.91 | 0.73 | −19% |
| 17 (inv) | 3 gsm | 170/175/180 | Z73-22 | 0.35 | 0.27 | −24% |
| 18 (inv) | 4 gsm | 170/175/180 | Z73-22 | 0.36 | 0.35 | −1% |
| 19 (inv) | 5 gsm | 170/175/180 | Z73-22 | 0.74 | 0.68 | −8% |
| 20 (comp) | 3 gsm | 160/170/180 | Z85B-40 | 0.81 | 0.28 | −65% |
| 21 (comp) | 4 gsm | 160/170/180 | Z85B-40 | 1.33 | 0.50 | −62% |
| 22 (comp) | 5 gsm | 160/170/180 | Z85B-40 | 1.77 | 0.88 | −50% |

The Fresh/Aged Peel Force Difference is calculated from the measured values:
Fresh/Aged Peel Force Difference = (Aged Peel Force − Fresh Peel Force)/Fresh Peel Force).

A negative value indicates a loss of Peel Force upon aging. The laminates of the invention demonstrated a better aging behavior than the comparative examples. The laminates of the invention may advantageously have a Fresh/Aged Peel Force Loss of less than 25%, as measured according to the Peel Force Measurement Method described herein.

Without wishing to be bound by theory, it is believed that the better aging behavior of the hot-melt formulation of the invention may be due the absence of a low molecular weight tackifier in the formulation (the tackifier can migrate into adjacent layers, which weakens the adhesive) as well as the crystalline character of the heterophase polymer of the inventive formulation (making it less accessible to the hydrophobic coating of the cellulose fibers which otherwise migrates into the adhesive).

Examples of Three-Dimensional Laminate, that May be Used as Part of a Backsheet

In the examples #23-29 below, the first layer was a 21 gsm carded air-through bonded nonwoven comprising 1.2 and 2 dpf phobic PE/PET fibers. The second layer was a 21 gsm carded air through nonwoven made of 2 dpf phobic PE/PET fibers. The hot-melt glue used for the invention examples was either 100% Licocene 2502 ("2502"), or a blend of 95 weight % Licocene 2502 with 5 weight % Licocene 6552 ("6552"), a maleic anhydride grafted polypropylene wax. The comparative example is a conventional tackifier-containing construction adhesive ("DM5813U", ex. Henkel).

The first layer and second layer were intermittently bonded and comprised apertures and protrusions. The Dry Peel Force and Wet Peel Force were measured as indicated before, and Dry/Wet Peel Force Difference calculated. A negative value indicates a Dry/Wet Peel Force Loss.

| Example # | Adhesive | Adhesive basis weight | Adhesive application temp, in ° C. (tank/pipe/gun) | Dry Peel Force | Wet Peel Force | Dry/Wet Peel Force Difference (%) |
|---|---|---|---|---|---|---|
| 23 (inv) | 2502 | 3 gsm | 130/135/140 | 0.18 | 0.18 | 0% |
| 24 (inv) | 2502 | 4 gsm | 130/135/140 | 0.19 | 0.19 | 0% |
| 25 (inv) | 2502 | 5 gsm | 130/135/140 | 0.34 | 0.31 | −9% |

-continued

| Example # | Adhesive | Adhesive basis weight | Adhesive application temp, in ° C. (tank/pipe/gun) | Dry Peel Force | Wet Peel Force | Dry/WetPeel Force Difference (%) |
|---|---|---|---|---|---|---|
| 26 (inv) | 95% 2502 + 5% 6252 | 3 gsm | 150/155/160 | 0.21 | 0.26 | +15% |
| 27 (inv) | 95% 2502 + 5% 6252 | 4 gsm | 150/155/160 | 0.28 | 0.27 | +4% |
| 28 (inv) | 95% 2502 + 5% 6252 | 5 gsm | 150/155/160 | 0.34 | 0.36 | +6% |
| 29 (comp) | DM5813U | 3 gsm | 160/170/180 | 0.27 | 0.19 | −30% |

Miscellaneous

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a wearer-facing side and an opposite garment-facing side, the article comprising a three-dimensional laminate, wherein the three-dimensional laminate comprises a first layer and a second layer;
    wherein the first layer is intermittently bonded to the second layer by a hot-melt adhesive so that the first layer comprises a plurality of protrusions not bonded to the second layer;
    wherein the three-dimensional laminate is configured to be liquid-permeable; and
    wherein the three-dimensional laminate is disposed on the wearer-facing side of the absorbent article and forms a liquid-permeable topsheet, such that the three-dimensional laminate is configured to be in contact with a wearer's skin during use of the absorbent article; and
    wherein the hot-melt adhesive consists essentially of a heterophase polymer having an enthalpy of fusion of at least 10 J/g, as measured according to the Enthalpy of Fusion Measurement Method.

2. The absorbent article of claim 1, wherein the heterophase polymer has an enthalpy of fusion of from about 15 J/g to about 40 J/g, as measured according to the Enthalpy of Fusion Measurement Method.

3. The absorbent article of claim 1, wherein the hot-melt adhesive has a storage modulus higher than $0.3 \times 10^6$ Pa at 37° C., as measured according to the Oscillatory Rheometry Test Method.

4. The absorbent article of claim 1, wherein the heterophase polymer comprises a propylene-ethylene copolymer.

5. The absorbent article of claim 1, wherein the first layer is a nonwoven layer and comprises from about 15% and up to 100% of natural fibers, by weight of the first layer.

6. The absorbent article of claim 5, wherein the natural fibers are cotton fibers.

7. The absorbent article of claim 1, wherein the hot-melt adhesive is disposed in a discontinuous application pattern between the first layer and the second layer.

8. The absorbent article of claim 1, wherein the second layer is a nonwoven comprising synthetic fibers.

9. The absorbent article of claim 8, wherein the second layer is selected from an air-through bonded carded nonwoven or a nonwoven comprising a meltblown layer.

10. The absorbent article of claim 1, wherein the three-dimensional laminate has a Dry Peel Force higher than 0.15N/50.8 mm, as measured according to the Peel Force Measurement Method.

11. The absorbent article of claim 1, wherein the three-dimensional laminate has a Dry/Wet Peel Force Loss of less than 50%, as measured according to the Peel Force Measurement Method.

12. The absorbent article of claim 1, wherein the three-dimensional laminate has a Fresh/Aged Peel Force Loss of less than 25%, as measured according to the Peel Force Measurement Method.

13. The absorbent article of claim 1, wherein the hot-melt adhesive is free of styrene block copolymers.

14. An absorbent article comprising a laminate disposed on a wearer-facing side of the article, wherein the laminate comprises a first layer and a second layer;
    wherein the first layer is intermittently bonded to the second layer by a hot-melt adhesive so that the first layer comprises a plurality of protrusions not bonded to the second layer;
    wherein the laminate is configured to be liquid-permeable;
    wherein the laminate forms a liquid-permeable topsheet, such that the laminate is configured to be in contact with a wearer's skin during use of the absorbent article;
    wherein the hot-melt adhesive consists essentially of a heterophase polymer; and
    wherein the hot-melt adhesive has a storage modulus higher than $0.3 \times 10^6$ Pa at 37° C., as measured according to the Oscillatory Rheometry Test Method.

15. The absorbent article of claim 14, wherein the heterophase polymer has an enthalpy of fusion of from about 15 J/g to about 40 J/g, as measured according to the Enthalpy of Fusion Measurement Method.

16. The absorbent article of claim 14, wherein the heterophase polymer comprises a propylene-ethylene copolymer.

17. The absorbent article of claim 14, wherein the first layer is a nonwoven layer and comprises from about 15% and up to 100% of natural fibers, by weight of the first layer.

* * * * *